United States Patent [19]

VandenBerg

[11] Patent Number: Plant 6,946

[45] Date of Patent: Jul. 25, 1989

[54] CHRYSANTHEMUM PLANT NAMED CLARO

[75] Inventor: Cornelis P. VandenBerg, Salinas, Calif.

[73] Assignee: Yoder Brothers, Inc., Barberton, Ohio

[21] Appl. No.: 210,002

[22] Filed: Jun. 22, 1988

[51] Int. Cl.[4] ..... A01H 5/00

[52] U.S. Cl. ..... Plt./77

[58] Field of Search ..... Plt./77

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A Chrysanthemum plant named Claro particularly characterized as to uniqueness by the combined characteristics of flat capitulum form; decorative capitulum type; white ray floret color; diameter across face of capitulum of up to 13 cm at maturity; uniform nine week photoperiodic flowering response to short days; medium plant height when grown as a pinched disbudded pot mum; and semi-spreading branching pattern.

3 Drawing Sheets

The present invention comprises a new and distinct cultivar of Chrysanthemum, botanically known as *Dendranthema grandiflora,* and referred to by the cultivar name Claro.

Claro, identified as 83-775001, was originated from a cross made in a controlled breeding program in Salinas, Calif. in 1983.

The female parent of Claro was the cultivar identified as Surf, disclosed in U.S. Plant Pat. No. 4,585. The male parent of Claro was an unnamed seedling, identified as 80-231006.

Claro was discovered and selected as one flowering plant within the progeny of the stated cross by Cornelis P. VandenBerg in Dec. 1983 in a controlled environment in Salinas, Calif.

The first act of asexual reproduction of Claro was accomplished when vegetative cuttings were taken from the initial selection in Mar. 1984 in a controlled environment in Salinas, Calif., by technicians working under formulations established and supervised by Cornelis P. VandenBerg.

Horticultural examination of controlled flowerings of successive plantings has shown that the unique combination of characteristics as herein disclosed for Claro are firmly fixed and are retained through successive generations of asexual reproduction.

Claro has not been observed under all possible environmental conditions. The phenotype may vary significantly with variations in environment such as temperature, light intensity, and daylength.

The following observations, measurements and comparisons describe plants grown in Salinas, Calif. and Leamington, Canada under greenhouse conditions which approximate those generally used in commercial greenhouse practice.

The following traits have been repeatedly observed and are determined to be basic characteristics of Claro, which, in combination, distinguish this Chrysanthemum as a new and distinct cultivar:

1. Flat capitulum form.
2. Decorative capitulum type.
3. White ray floret color.
4. Diameter across face of capitulum up to 13 cm at maturity.
5. Uniform nine week photoperiodic flowering response to short days.

6. Medium plant height, requiring 0 to 7 long days after pinch prior to short days and 1 application of 2500 ppm B-9 SP to attain a flowered plant height of 25 to 35 cm for year-round flowerings when grown as a pinched disbudded pot mum.
7. Semi-spreading branching pattern.

The accompanying photographic drawings show typical inflorescence and leaf characteristics of Claro, with the colors being as nearly true as possible with illustrations of this type.

Sheet 1 is a color photograph of Claro grown as a pinched disbudded pot mum.

Sheet 2 is a black and white photograph of three views of the inflorescence of Claro.

Sheet 3 is a black and white photograph showing the upper and under sides of the leaves of Claro at three stages of development (mature, intermediate and immature).

Of the commercial cultivars known to the inventor, the most similar in comparison to Claro is Mountain Snow, disclosed in U.S. Plant Pat. No. 3,215. Reference is made to attached Chart A, which compares certain characteristics of Claro to the same characteristics of Mountain Snow. Similar traits are ray floret color, capitulum form and type, branching pattern, and plant height. Claro has a slightly smaller capitulum diameter and a faster flowering response. In addition, Claro has darker foliage and better durability of foliage than Mountain Snow. Under adverse conditions Mountain Snow develops bract tissue in the center of the capitulum. Claro does not develop bract tissue.

In the following description, color references are made to The Royal Horticultural Society Colour Chart. The color values were determined on plant material grown in Salinas, Calif. on Mar. 14, 1988.

Classification:

*Botanical.*—*Dendranthema grandiflora,* cv. Claro.

*Commercial.*—Decorative disbud pot mum.

INFLORESCENCE

A. Capitulum:

*Form.*—Flat.

*Type.*—Decorative.

*Diameter across face.*—Up to 13 cm at maturity.

B. Corolla of ray florets:

*Color (general tonality from a distance of three meters).*—White.

*Color (upper surface).*—155D, with center 150D.

*Color (under surface).*—155D.

*Shape.*—Crossection: Concave. Longitudinal: Slightly incurved, slightly ribbed.

C. Corolla of disc florets:

*Color (mature).*—Closest to 144B.

*Color (immature).*—Closest to 144B. Very few disc florets, covered by the incurved center rows of ray florets.

D. Reproductive organs:

*Androecium.*—Present on disc florets only; very scant pollen.

*Gynoecium.*—Present on both ray and disc florets.

PLANT

A. General appearance:

*Height.*—Medium; 25 to 35 cm as a pinched disbudded pot mum with 0 to 7 long days after pinch prior to short days and 1 application of 2500 ppm B-9 SP.

*Branching pattern.*—Semi-spreading and prolific.

B. Foliage:

*Color (upper surface).*—137A.

*Color (under surface).*—137B.

*Shape.*—Lobed and slightly serrated.

CHART A

COMPARISON OF CLARO AND MOUNTAIN SNOW

| | Claro | Mountain Snow |
|---|---|---|
| Ray floret color | White | White |
| Capitulum form | Flat | Flat |
| and type | Decorative | Decorative |
| Branching pattern | Semi-spreading | Semi-spreading |
| Diameter across face of capitulum | Up to 13 cm | Up to 15 cm |
| Plant height | Medium | Medium |
| Flowering response period | 9 weeks | 10 weeks |

COMPARISONS MADE OF PLANTS GROWN AS PINCHED DISBUDDED POT MUMS IN SALINAS, CALIFORNIA AND IN LEAMINGTON, CANADA

I claim:

1. A new and distinct Chrysanthemum plant named Claro, as described and illustrated.

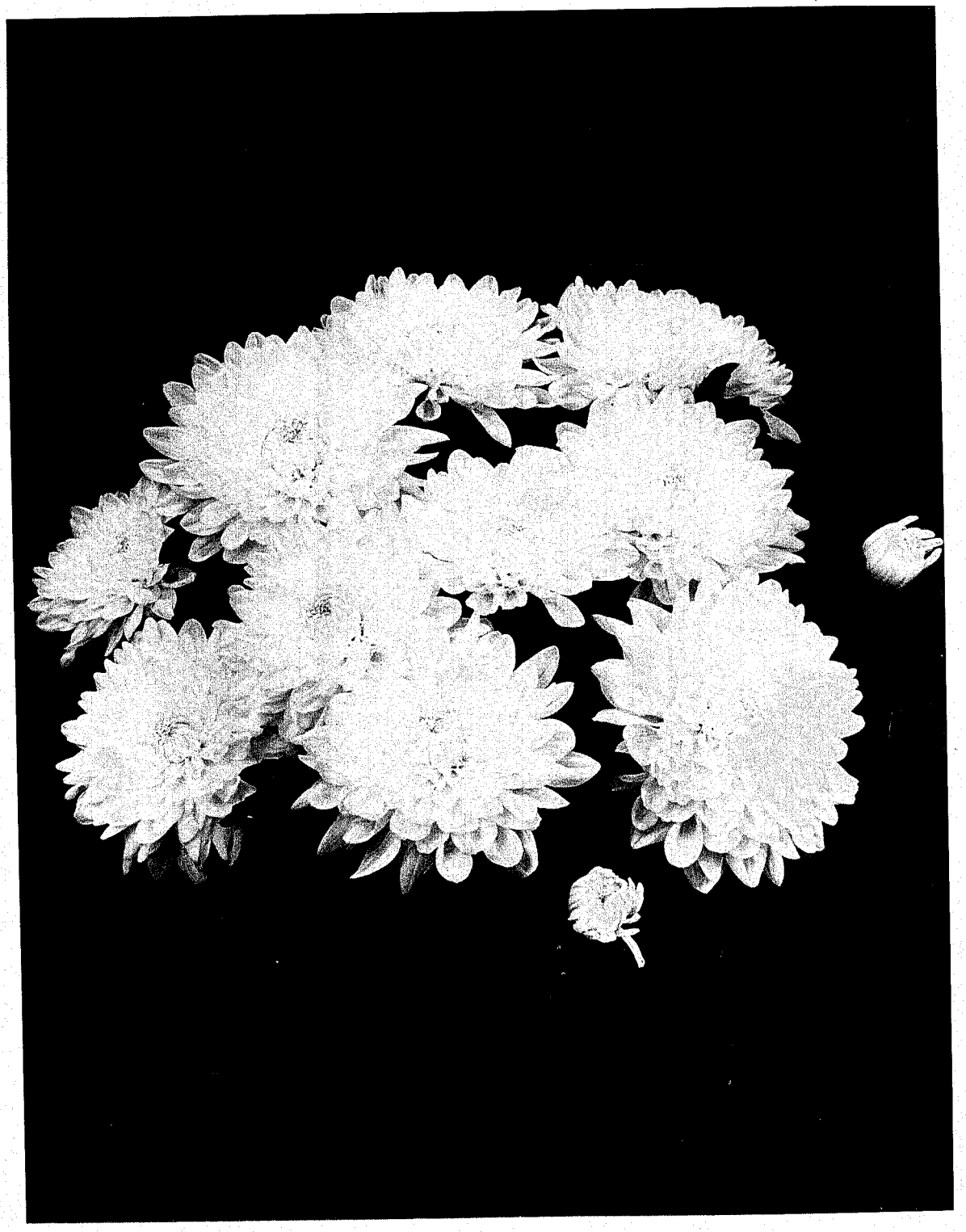

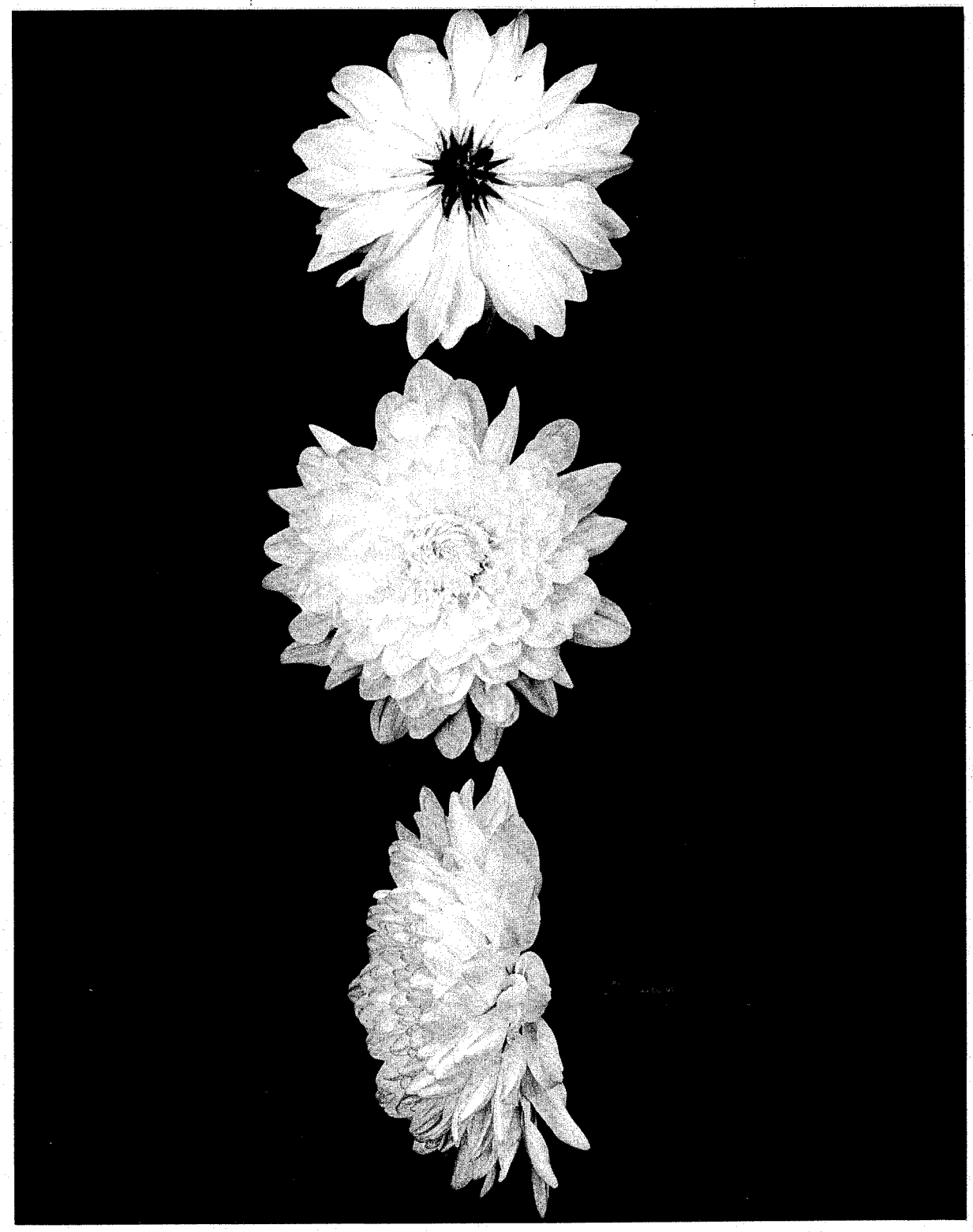

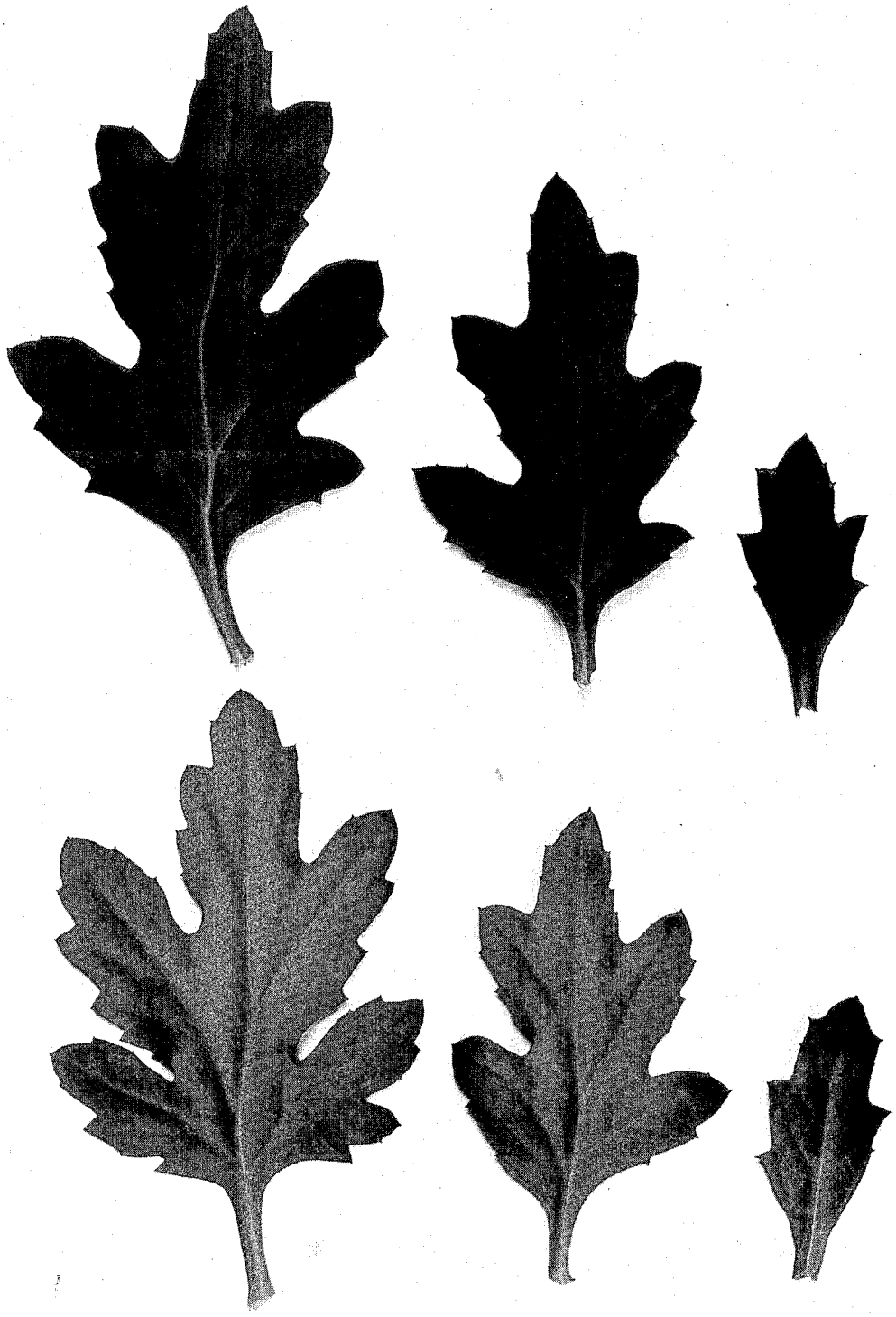

* * * * *